(12) United States Patent
Stangenes et al.

(10) Patent No.: US 8,532,743 B2
(45) Date of Patent: Sep. 10, 2013

(54) MOVABLE MAGNET FOR MAGNETICALLY GUIDED CATHETER

(75) Inventors: Todd R. Stangenes, Minneapolis, MN (US); Saurav Paul, Minneapolis, MN (US); James V. Kauphusman, Champlin, MN (US); Troy T. Tegg, Elk River, MN (US); Jeffrey A. Schweitzer, St. Paul, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 326 days.

(21) Appl. No.: 12/851,407

(22) Filed: Aug. 5, 2010

(65) Prior Publication Data

US 2012/0035460 A1  Feb. 9, 2012

(51) Int. Cl.
- *A61B 5/05* (2006.01)
- *A61M 25/00* (2006.01)
- *A61M 31/00* (2006.01)

(52) U.S. Cl.
USPC ............ 600/424; 600/435; 604/510; 604/528

(58) Field of Classification Search
None
See application file for complete search history.

(56) References Cited

U.S. PATENT DOCUMENTS

| | | | | |
|---|---|---|---|---|
| 3,514,081 | A * | 5/1970 | Cavanaugh et al. | 366/342 |
| 5,776,080 | A * | 7/1998 | Thome et al. | 600/585 |
| 6,126,647 | A * | 10/2000 | Posey et al. | 604/270 |
| 6,129,685 | A * | 10/2000 | Howard, III | 600/585 |
| 6,542,766 | B2 * | 4/2003 | Hall et al. | 600/374 |
| 6,662,034 | B2 * | 12/2003 | Segner et al. | 600/373 |
| 6,817,364 | B2 * | 11/2004 | Garibaldi et al. | 128/899 |
| 6,980,843 | B2 * | 12/2005 | Eng et al. | 600/374 |
| 7,017,584 | B2 * | 3/2006 | Garibaldi et al. | 128/899 |
| 7,066,924 | B1 * | 6/2006 | Garibaldi et al. | 604/510 |
| 7,341,063 | B2 * | 3/2008 | Garbibaldi et al. | 128/899 |
| 7,346,379 | B2 * | 3/2008 | Eng et al. | 600/374 |
| 7,431,726 | B2 * | 10/2008 | Spence et al. | 606/151 |
| 8,196,590 | B2 * | 6/2012 | Sabo et al. | 128/899 |
| 2002/0019644 | A1 * | 2/2002 | Hastings et al. | 606/159 |
| 2002/0058866 | A1 * | 5/2002 | Segner et al. | 600/374 |
| 2004/0236367 | A1 * | 11/2004 | Brown et al. | 606/194 |
| 2004/0260172 | A1 * | 12/2004 | Ritter et al. | 600/411 |
| 2005/0043611 | A1 * | 2/2005 | Sabo et al. | 600/411 |
| 2006/0144407 | A1 * | 7/2006 | Aliberto et al. | 128/899 |
| 2007/0049846 | A1 * | 3/2007 | Bown et al. | 600/585 |
| 2007/0197891 | A1 * | 8/2007 | Shachar et al. | 600/374 |
| 2008/0091193 | A1 * | 4/2008 | Kauphusman et al. | 606/41 |
| 2010/0174177 | A1 * | 7/2010 | Wu | 600/424 |
| 2012/0035466 | A1 * | 2/2012 | Tegg | 600/424 |
| 2012/0035539 | A1 * | 2/2012 | Tegg | 604/95.01 |
| 2012/0035605 | A1 * | 2/2012 | Tegg et al. | 606/41 |
| 2012/0221001 | A1 * | 8/2012 | Tegg et al. | 606/41 |

* cited by examiner

*Primary Examiner* — Long V. Le
*Assistant Examiner* — Angela M Hoffa
(74) *Attorney, Agent, or Firm* — Trenner Law Firm LLC

(57) ABSTRACT

A catheter is disclosed having a flexible tubing with a proximal end and a distal end. The catheter comprising at least one movable magnet provided within the distal end of the flexible tubing. A control mechanism is operable to selectively activate the at least one movable magnet from the proximal end of the flexible tubing. The at least one movable magnet is responsive to an external magnetic field to position and guide the distal end of the flexible tubing within a body of a patient.

20 Claims, 6 Drawing Sheets

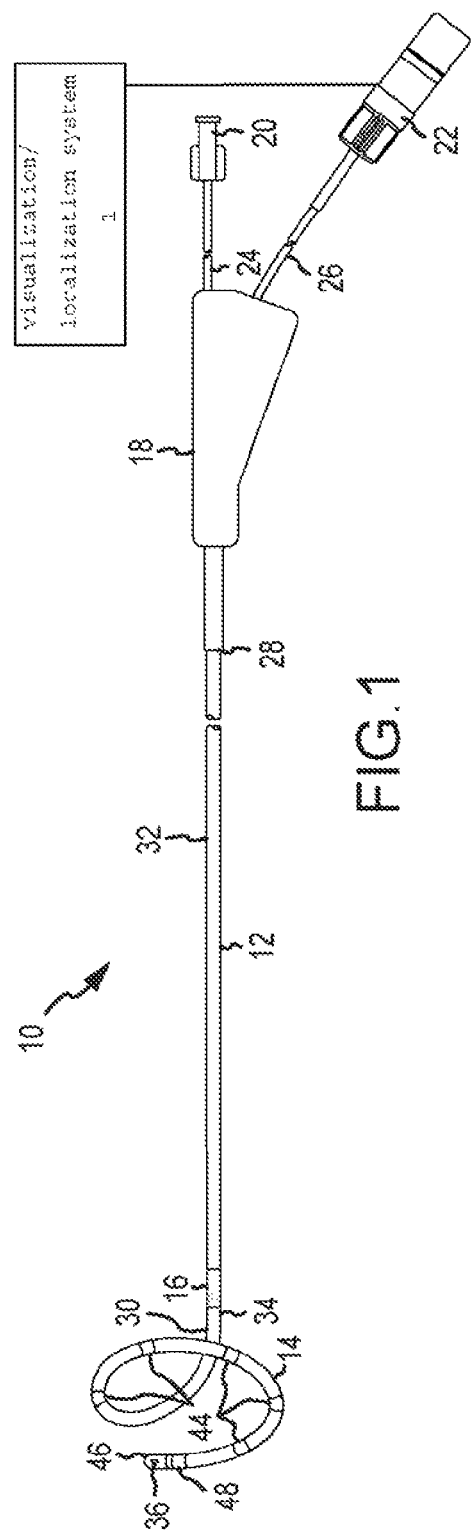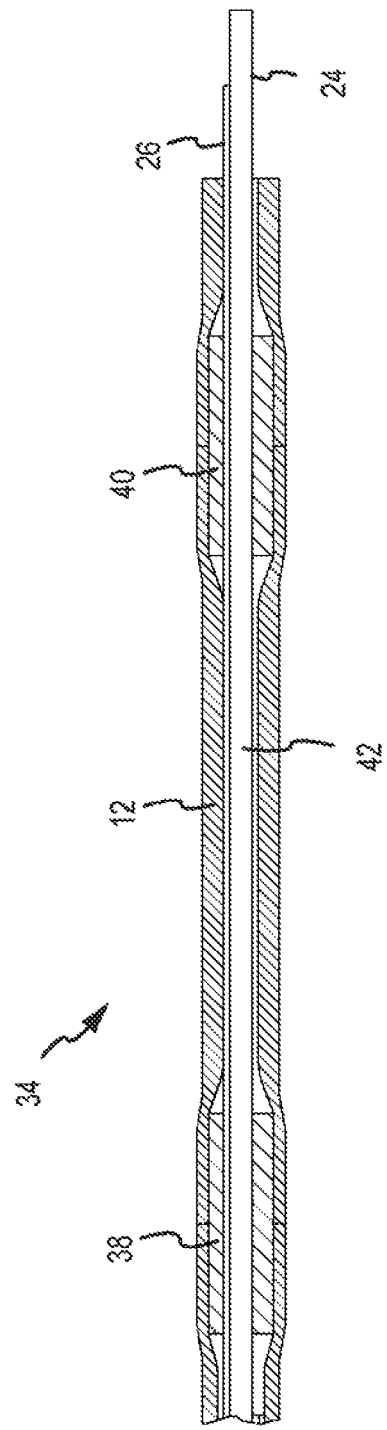

МОVABLE MAGNET FOR MAGNETICALLY GUIDED CATHETER

BACKGROUND OF THE INVENTION a. Field of the Invention

This invention relates generally to medical instruments, and, more specifically, to a navigable catheter device positionable within a body of a patient using a movable magnet.

b. Background Art

Catheters are flexible, tubular devices that are widely used by physicians performing medical procedures to gain access into interior regions of the body. Careful and precise positioning of the catheters within the body is important to successfully completing such medical procedures. This is particularly so when catheters are used to produce emissions of energy within the body during tissue ablation procedures. Conventionally, positioning of such catheters was accomplished with mechanically steerable devices. More recently, magnetically navigable catheter devices have been developed that are navigated with an externally applied magnetic field. Such catheter devices can be complex in their construction, and therefore are difficult to manufacture and relatively expensive to produce.

Magnetic stereotactic systems have been developed that are particularly advantageous for positioning of catheters, as well as other devices, into areas of the body that were previously inaccessible or at least difficult to access. The magnetic fields and gradients are generated to precisely control the position of the catheter within the patient's body. Once correctly positioned, physicians may operate the catheter, for example, to ablate tissue to interrupt potentially pathogenic heart rhythms or to clear a passage in the body, for example. Specifically, such stereotactic systems monitor the position of a tip of the catheter in response to the applied magnetic fields using well established feedback and control algorithms the catheter tip may be guided to and positioned in a desired location within the patient's body.

The magnetic response of the catheter can be a limitation on the precise control of a catheter when used with such magnetic guidance systems. Improvements in catheters utilized with magnetic guidance and control systems, such as stereotactic systems, are desired. Specifically, a low cost, yet high performance magnetically guided catheter is desirable.

BRIEF SUMMARY OF THE INVENTION

In various embodiments, magnetic guided catheters are disclosed that provide high performance when used with, for example, magnetic stereotactic systems.

In one embodiment, a catheter is provided having a flexible tubing with a proximal end and a distal end. The catheter comprising at least one movable magnet provided within the distal end of the flexible tubing. A control mechanism is operable to selectively activate the at least one movable magnet from the proximal end of the flexible tubing. The at least one movable magnet is responsive to an external magnetic field to position and guide the distal end of the flexible tubing within a body of a patient.

In another embodiment, a catheter is provided having a flexible tubing with a proximal end and a distal end. At least one magnet is provided within the flexible tubing. A control mechanism is operable to move the at least one magnet within the flexible tubing. The movement effected from the proximal end of the flexible tubing. The catheter also includes an active area of the flexible tubing. The at least one magnet is moveable into the active area of the flexible tubing, and the at least one magnet responsive to an external magnetic field in the active area of the flexible tubing to position and guide the distal end of the flexible tubing within a body of a patient.

In yet another embodiment, a method of guiding a catheter is provided. The method comprising: providing at least one movable magnet within a flexible tubing of the catheter; selectively activating the at least one movable magnet from a proximal end of the flexible tubing; and applying an external magnetic field to the at least one magnet to position a distal end of the flexible tubing within a body of a patient.

Still other features of magnetic guided catheters are disclosed.

BRIEF DESCRIPTION OF THE DRAWINGS

FIG. 1 illustrates an exemplary magnetic guided catheter with a movable magnet.

FIG. 2 is a magnified cross sectional view of a portion of the catheter shown in FIG. 1, showing exemplary stationary magnets that may also be implemented.

DETAILED DESCRIPTION OF THE INVENTION

Figure 3:
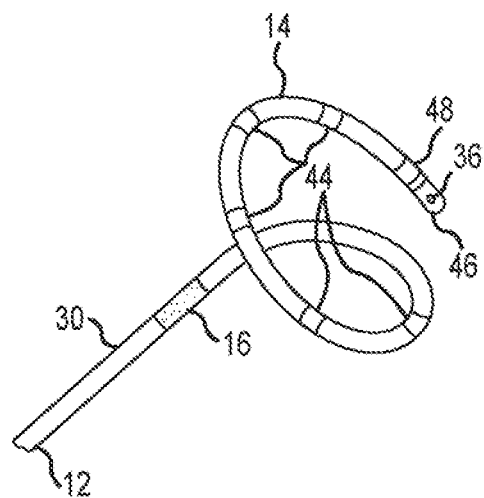
FIG. 3 is a magnified isometric view showing the movable magnet shown in FIG. 1 in the distal end near the tip assembly of the catheter.

Many specific details of certain embodiments of the invention are set forth in the following description in order to provide a thorough understanding of such embodiments. One skilled in the art, however, will understand that the present invention may have additional embodiments, or that the present invention may be practiced without several of the details described in the following description.

Exemplary embodiments may employ any of a wide variety of different types and configurations of catheters. In one example, the invention may be implemented as an introducer which may be positioned at the target location inside the patient's body and then used for placing of a catheter for carrying out the medical procedure. In other examples, a magnetically guided catheter may be a standard linear catheter. As will become apparent from the following description, the invention may be implemented with a single catheter, or with multiple (e.g., two or more) catheters that are utilized in conjunction with one another for mapping and/or other medical procedures. In still other examples, the magnetically guided catheter may be implemented as a shaped (e.g., curvilinear) catheter, and in addition to one or more magnets, may also include one or more of electrodes (e.g., for ablation and/or mapping procedures), temperature sensors, and/or irrigation ports. These and other examples will be readily understood by one having ordinary skill in the art after becoming familiar with the teachings herein.

By way of a specific example, FIG. 1 illustrates a first exemplary non-steerable, single-use magnetically guided catheter 10 generally including a flexible outer tube (or tubing) 12, a tip assembly 14, at least one movable positioning magnet 16, a Y connector 18, a luer device 20, and an electrical connector 22. Electrical connector 22 may be provided to establish electrical connection with a power source (not shown) that operates electrodes of tip assembly 14 to perform, for example, ablation procedures, mapping or pacing procedures, or to perform other aspects of a medical procedure.

Although it will become evident that aspects of exemplary catheter 10 are applicable to a variety of medical procedures and end uses, the invention will be described principally in the context of a specific example of the magnetically guided catheter 10 shown in FIG. 1. Specifically, catheter 10 is believed to be particularly advantageous as an ablation catheter for creating endocardial lesions during cardiac ablation procedures to treat arrhythmias, and also for cardiac electrophysiological mapping and delivering diagnostic pacing stimuli. However, the invention and the appended claims are not intended to be limited to any specific example, including but not limited to specific examples or embodiments described herein, except when explicitly defined as such in the appended claims.

Y-connector 18 separates an inner tube 24 from electrical lead wires 26 extending between tip assembly 14 and electrical connector 22. More specifically, tube 24 and the lead wires forward of Y-connector 18 pass internally through outer tube 12, while aft of Y-connector 18, inner tube 24 and leads for the lead wires 26 are exposed and separated for connection to a fluid source (not shown) and the power source (not shown), respectively. In one embodiment, electrical connector 22 is a known connector configured to engage the power source or a power supply with, for example, a plug-in connection. One suitable electrical connector is a 14-pin REDEL® plastic connector commercially available from LEMO of Rohnert Park, Calif., although other connectors from various manufacturers may likewise be utilized.

Outer tube 12 includes a proximal end 28 coupled to Y-connector 18, a distal end 30 coupled to tip assembly 14, and an axial length extending between proximal end 28 and distal end 30. In one embodiment, flexible tubing 12 is fabricated according to known processes, such as multilayer processing including extrusion processes, mandrel-based processes and combinations thereof from any suitable tubing material known in the art of medical instruments, such as engineered nylon resins and plastics, including but not limited to PEBAX® tubing of Ato Fina Chemicals, France.

Although not required, in an exemplary embodiment, tubing 12 is fabricated from a first tubing material defining a first portion 32 of tubing 12 more proximal the Y connector 18, and the tubing 12 is fabricated from a second tubing material defining a second portion 34 of tubing 12 more proximal the tip assembly 14. Additional tubing material may be used to define other portions of tubing 12, and even the tip assembly 14. By fabricating first portion 32, second portion 34, and/or other portions from different materials and/or grades of materials, tubing 12 may have varying flexible properties, and is sometimes referred to as a multi-flexible tube.

For example, in one embodiment, the first material defining first portion 32 of tubing 12 is a comparatively rigid and kink resistant braided material. First portion 32 is formed with different portions of braided material, semi-soft material, and soft material fused to one another so that first portion 32 becomes increasingly flexible along the axial length as first portion 32 approaches tip assembly 14. The second material defining second portion 34 of tubing 12 is a softer material having flexible properties. In the illustrated embodiment, each of the tubing portions 32, 34 share a common outside diameter of, for example, 7 French, although in other embodiments, tubing portions 32, 34 may have varied diameters.

As shown in FIG. 1, first portion 32 extends for a majority of the axial length of tubing 12 between proximal end portion 28 and distal end portion 30. Second portion 34 of tubing 12 extends for a shorter length than the length of first portion 32. By way of example only, in a specific embodiment first portion 32 extends for an axial length of about 126.3 cm, and second portion 34 extends for an axial length of about 2.2 cm, although other relative lengths of the tube portions may likewise be employed in other embodiments. The different relative lengths of tube portions 32, 34, as well as the different flexible properties of tube portions 32, 34, allow tip assembly 14 to be more precisely positioned within a patient's body, while also avoiding problems of kinks and excessive deflection of tubing 12 along the majority of its length during use and handling.

In operation, a distal end portion 30 of catheter 10, including tip assembly 14, is navigated to a site in the body where a medical procedure, such as an atrial mapping, pacing and/or ablation are to occur. Distal end portion 30 may extend, for example, into a heart chamber of a patient. Once distal end portion 30 is in the heart chamber, the positioning magnet 16 may be moved to the desired position within tubing 12 and/or tip assembly 14. A magnetic field is applied so that the positioning magnet 16 provides an orienting force to distal end portion 30, causing the positioning magnet 16 to respond to the applied magnetic field and flex tubing portion 34 to precisely position tip assembly 14 for performance of the procedure at a specific location.

The magnetic fields used to orient tip assembly 14 are, in one embodiment, generated with a magnetic stereotactic system (not shown). Such stereotactic systems are known and are commercially available from, for example, Stereotaxis of St. Louis, Mo. Such systems may include movable source magnets outside the body of the patient, and operative details of such systems are disclosed in, for example, U.S. Pat. Nos. 6,475,223 and 6,755,816, the disclosures of which are hereby incorporated by reference in their entirety. While catheter 10 is advantageous for use with a stereotactic system, it is contemplated that magnetic fields and gradients to position catheter tip assembly 14 may alternatively be generated by other systems and techniques if desired.

FIG. 2 is a magnified view of the second portion 34 at the distal end 30 of catheter 10 shown in FIG. 1. FIG. 2 shows optional stationary magnets 38 and 40 which may be provided at one or more locations along tubing 12 (and are not limited to second portion 34). Magnets 38 and 40 may be permanent magnets, for example, neodymium-iron boron-45 (NdFeB-45) formed into an elongated tubular shape, and having a central bore formed therethrough. Heat shrink techniques or adhesives may also be utilized to permanently attach magnets 38 and 40 to tubing 12.

In an exemplary embodiment, inner tube 24 defines a central lumen 42 extending through each tube portion 32, 34, and also through central bores formed in the stationary magnets 38 and 40. Inner tube 24 has an outer diameter that is smaller than an inner diameter of tubing 12 and its portions 32, 34 such that space extends between an outer surface of inner tube 24 and an inner surface of tubing 12. In one embodiment, this space is used to accommodate lead wires 26 for electrical components of the tip assembly 14. For example, lead wires 26 for a temperature sensor 48 (shown in tip assembly 14 in FIG. 1) may pass through a space defined by the recess in magnets 38 and 40. For purposes of example, where the temperature sensor is a thermocouple type temperature sensor, the lead wires may be, for example, 38 AWG wires having quad polyimide insulation.

FIG. 3 is a magnified isometric view of the distal end 30 of the catheter 10 shown in FIG. 1, showing the movable magnet 16 and tip assembly 14. Tip assembly 14 may be more rigid than flexible tubing 12, e.g., in order to maintain a predetermined shape. In that regard, tip assembly 14 may have any suitable shape, e.g., as provided at least in part using a forming wire. Although the tip assembly 14 is shown and described herein having a generally helical shape, other configurations may also be used. For example, an in-line configuration (not shown) may be used, wherein the tip assembly 14 is straight and generally linear along a longitudinal axis. In any event, tip assembly 14 is a generally flexible member that can be flexed, and can bend or deflect along its axial length, for example, to different operating positions, based at least in part on a response to the magnetic field applied to the movable magnet 16.

Tip assembly 14 may also include multiple electrode elements, such as ring electrodes 44 for electrophysiological mapping purposes, spaced from one another by dielectric materials as is known in the art. Tip assembly 14 may also include a tip electrode 46, and a temperature sensor 48. The tip electrode 46 may be connected to the end of tip assembly 14. Band electrodes 44 and temperature sensor 48 are, in one embodiment, attached to an outer surface of tip assembly 14. Lead wires extend to the band electrodes 44, the tip electrode 46, and temperature sensor 48 on first respective ends thereof, and to electrical connector 22 (shown in FIG. 1) on second ends so that the electrodes and temperature sensor may be energized by a power source (not shown), and data may be provided for the user.

In an exemplary embodiment, the band electrodes 44 are 5-7 Fr ring-shaped band electrodes that is, for example, 2 mm in length, and spaced from the tip electrode 46 by a predetermined distance of 2 mm. The tip electrode 46 may be, for example an 8 Fr hemispherical-shaped tip electrode that is 2 mm in length. In other embodiments, other sizes of electrodes 44, 46 may be utilized, including but not limited to 4 mm or 8 mm electrodes. In the exemplary embodiment, the electrodes 44, 46 are fabricated from 90% platinum and 10% iridium, or other materials known in the art such that the electrodes are viewable under fluoroscopic exposure. Each of the electrodes 44, 46 may also include multiple electrode elements for electrophysiological mapping purposes as is known in the art.

Tip assembly 14 is shown having five band electrodes 44 and one tip electrode 46. Of course, more or fewer electrodes may be implemented for mapping and/or ablation of myocardial tissue. In addition, the catheter may also be 'tracked' (localized position, configuration of shaft, and/or orientation) using magnetically-activated coils, such as those commercially available from Biosense Webster (e.g., the Carto system) or St. Jude Medical (e.g., the MediGuide magnetic position and orientation, or P&O, system), or with the St. Jude Medical EnSite NavX-compatible electrodes disposed along the length of the catheter shaft. That is, the magnets may be activated using an external magnetic field such that the magnets are visible on a display device. Accordingly, the tip assembly 14 (and any other part of the catheter the magnets may be placed or moved to) can be depicted on the display along with a rendition of the target tissue, for more accurate placement without the need for fluoroscopy.

In an example, the visualization/localization system 1 (illustrated diagrammatically in FIG. 1) operatively associated with the catheter 10) may include at least one of a magnetic resonance imaging (MRI) system, an electromagnetically-based or an impedance-based visualization/localization system, and/or a fluoroscopically-based imaging system may be configured to detect the flexible tubing and the at least one magnet. The movable magnet comprises an electromagnet switchable from an active state to an inactive state relative to the external magnetic field, wherein the external magnetic field is coordinated with the MRI system, the electromagnetically-based or the impedance-based visualization/localization system and/or the fluoroscopically-based imaging system.

Tip assembly 14 is particularly well suited for ablation procedures wherein electrodes 44 and 46 are energized to deliver radio frequency waves at the site of an abnormal electrical pathway in the body. Radiofrequency (RF) energy may therefore be applied to biological tissue in proximity to tip assembly 14. Ablation procedures are typically used, for example, within the interior chambers of the heart to thermally ablate cardiac tissue. Electrodes 44 and 46 may additionally be operated to record intracardiac signals and to provide pacing signals.

In one embodiment, a tip positioning magnet (not shown) may be embedded within the end portion of the tip assembly 14. The tip positioning magnet may be a generally cylindrical shaped permanent magnet fabricated from a known magnetic material, such as neodymium-iron boron-45 (NdFeB-45). Of course the design is not so limited, and tip positioning magnet may be formed from other materials and may have different shapes.

The movable magnet 16 is shown in FIG. 3 in the distal end portion 30 of the catheter 10 and may be moved through tubing 12 and/or tip assembly 14. Moveable magnet 16 may be, for example, neodymium-iron boron-45 (NdFeB-45) formed into an elongated tubular shape. A control mechanism may be operable by the user to selectively position and activate the movable magnet 16 for positioning at various locations on an as-needed or as-desired basis. In an exemplary embodiment, the movable magnet 16 may be positioned by the user from the proximal end 28 of the flexible tubing 12, e.g., at connector 18 when implemented as a handle. The moveable magnet 16 is responsive to an external magnetic field and can be used to position and guide the tip assembly 14 and/or the distal end 30 of the flexible tubing 12 within a body of a patient.

Figure 4:
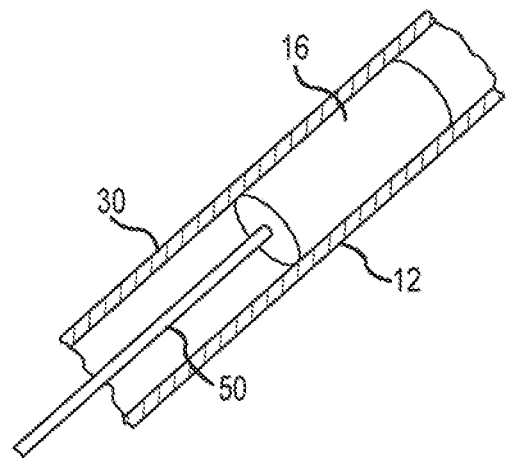
FIG. 4 is a magnified cross sectional view of the distal end of the catheter as shown in FIG. 3, showing the movable magnet in more detail.

In an exemplary embodiment, the control mechanism includes a tether 50 (e.g., a wire) connected on one end to the magnet 16, and provided through the lumen 42 of the tubing 12 outside of the patient's body. FIG. 4 is a magnified cross sectional view of the distal end 30 of the catheter 10 shown in FIG. 3, showing the tether 50 connected to the movable magnet 16. The tether 50 may be sufficiently stiff so as to enable pushing and pulling of the movable magnet 16 from outside of the patient's body. Exemplary positioning of the movable magnet 16 is illustrated in FIGS. 5A-B.

Although the control mechanism is illustrated as a tether 50, other control mechanisms are also contemplated. For example, another manually operated control mechanism may also include a reel that can be rotated to push the tether 50 in a first direction (as illustrated by arrow 52 in FIG. 5A) toward the distal end 30 of the catheter 10. The reel can also be rotated the opposite direction to pull the tether 50 in a second direction toward the proximal end 28 of the catheter 10 (e.g., as illustrated by arrow 54 in FIG. 5B). Automated control mechanisms may also be provided, including, but not limited to, motor-driven devices which respond to signals from a computer or other electronic device.

Figure 5B:
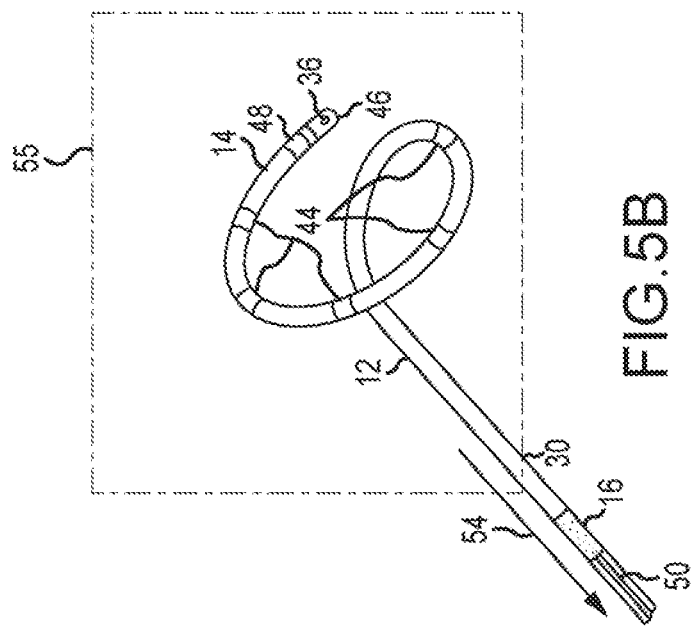
FIGS. 5A-B are magnified isometric views of the distal end of the catheter as shown in FIG. 3, further illustrating the movable magnet moving between a more distal position in FIG. 5A and in a more proximal position in FIG. 5B.
Figure 5A:
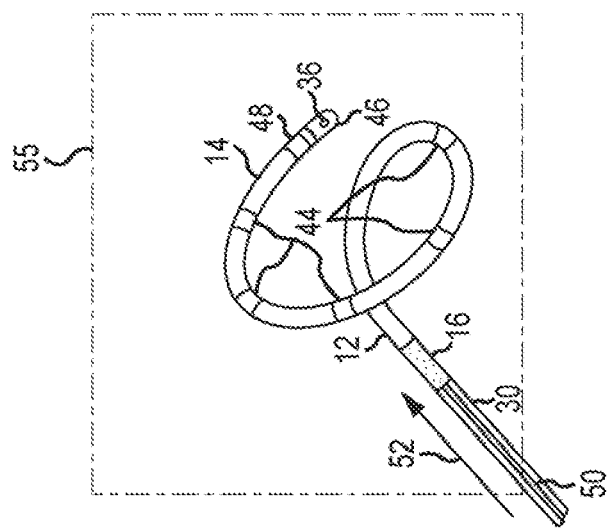

Also shown in FIGS. 5A and 5B is an external magnetic field 55 which may be implemented to position and guide the distal end 30 of the flexible tubing 12 within a body of a patient. In an exemplary embodiment, the external magnetic field 55 may be a constant application, wherein the movable magnet 16 is activated by positioning the movable magnet 16 within the external magnetic field (FIG. 5A), and deactivated by positioning the movable magnet 16 outside of the external magnet field (FIG. 5B).

Figure 6C:
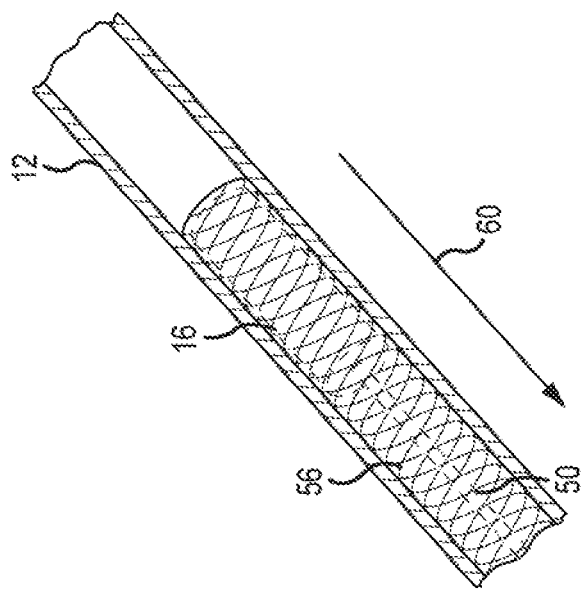
FIGS. 6A-C are magnified cross sectional views of the distal end of the catheter as shown in FIG. 3, further illustrating movement of the movable magnet relative to a shielded area.
Figure 6B:
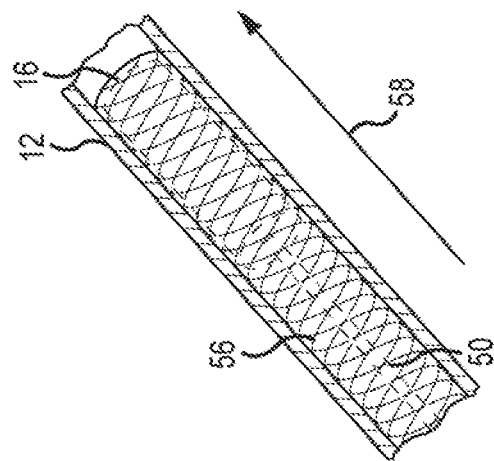
Figure 6A:
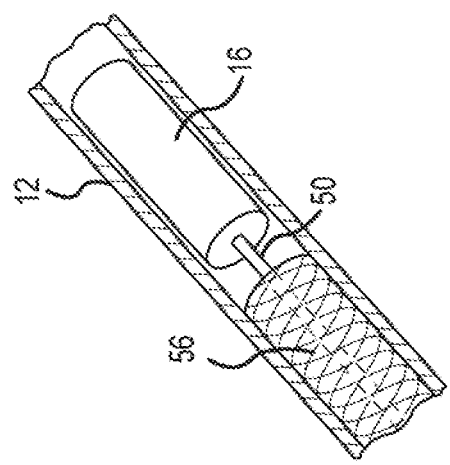

The movable magnet 16 may also be activated/deactivated using one or more shields or shielded areas 56 in the catheter 10, thereby shielding the magnet 16 from the external magnetic field. FIGS. 6A-C are magnified cross sectional views of the distal end portion 30 of catheter 10, illustrating relative movement of the movable magnet 16 and the shielded area 56. The movable magnet 16 is shown positioned outside of the shielded area 56 in FIG. 6A (in an activated state).

In one example shown in FIG. 6B, the movable magnet 16 may be moved inside of the shielded area 56 by moving the shielded area 56 over the movable magnet 16, as illustrated by arrow 58. In another example shown in FIG. 6C, the shielded area 56 is instead moved over the movable magnet 16, as illustrated by arrow 60. In another example, not shown, both the movable magnet 16 and the shielded area 56 may be moved together to effect shielding. In any case, positioning the movable magnet 16 inside the shielded area 56 de-activates a response from the movable magnet 16, and positioning the movable magnet 16 outside the shielded area 56 activates a response from the movable magnet 16.

Once the catheter 10 is positioned with the tip assembly 14 at the desired location in a patient's body, the movable magnet 16 may be activated. Activating the magnet may be by applying an external magnetic field (FIGS. 5A-B), and/or by moving the movable magnet 16 into the external magnetic field. In any event, applying an external magnetic field may cause a bending and/or pulling force on the tubing 12 and/or tip assembly 14 of the catheter 10 to enable better positioning at the desired location in the patient's body (e.g., adjacent the cardiac tissue to be mapped or ablated).

If a magnetic field is applied to multiple catheters in the patient, or to multiple magnets in the same catheter, all of the magnets will respond to the magnetic field. However, by positioning the magnets and/or shielding the magnets according to the embodiments described above, the magnets may be selectively activated/de-activated for more precise control.

It should be noted that shielding the magnet may include physically inhibiting movement of the magnet in response to the external magnetic field, thereby providing a mechanical alternative. That is, the mechanical shield (or covering) advanced over the magnet can be made sufficiently rigid that the magnetic field is unable to move the magnet. This could be accomplished, for example, through the use of a rigid tube or a tensioning cable strung through discrete segments along the shaft. Alternatively, the magnet may be moved to a location in the shaft that is sufficiently rigid that it would essentially be out of the magnetic field.

Also advantageously, in addition to positioning the catheter 10, the embodiments described herein enable the user to achieve different shapes/curves of the catheter 10. For example, removing one of multiple magnets, or repositioning a magnet after it has been activated (e.g., in a rigid portion of the catheter) and then re-activating the magnet (e.g., in a more flexible portion of the catheter) creates a deflection in the tubing 12 and can form a curved shape.

After the catheter 10 has been positioned at the desired location within the patient's body, and the movable magnet 16 and/or shielding 56 are no longer needed or desired, one or both of the movable magnet 16 and/or the shielding 56 may be withdrawn through the tubing 12 of the catheter 10. For example, withdrawing the movable magnet 16 and/or the shielding 56 may be desired so that other tubing and/or components may instead be inserted through the tubing 12 for the medical procedure.

It will be readily apparent to those having ordinary skill in the art after having become familiar with the above teachings that the catheter 10 may also be provided such that at least one magnet is operable to automatically or "robotically" (i.e., without user intervention) position at least a portion of the flexible tubing within the body of the patient. In an exemplary embodiment, a sheath of the catheter may be driven using a pinch roller which pushes the sheath linearly into the patient's body for gross positioning of the catheter 10. Pinch rollers may be readily implemented instead of a handle for the catheter using a standard introducer-type sheath having a metallic (e.g., flat wire) braiding. Pinch rollers are known and therefore are not shown in the drawings.

Once the sheath has been grossly positioned in the patient's body, a magnet may be activated (e.g., as already described above) to fine tune positioning of the catheter 10 within a particular area of the patient's body (e.g., in the heart). In one example, the magnet may be a part of or "fixed" in the sheath. In another example, the magnet may be provided separately once the sheath has been grossly positioned within the patient's body. The magnet may be provided as a "ring" magnet having an outer diameter substantially the same size as the inner diameter of the sheath. In another example, the magnet may be provided within the sheath using another lumen with the magnet, so that the magnet is provided substantially co-axial to the sheath.

The magnet may be moved to various locations in the sheath, and the magnet activated using an external magnetic field to position various portions of the sheath at desired locations within the patient's body. In one example, a feedback loop may be provided to a computer-controlled system which executes program code for determining the position of a magnet relative to the sheath, and the sheath relative to the target tissue within the patient's body. An algorithm maps the tissue geometry, and moves the magnet to different positions within the sheath while activating and de-activating the external magnetic field, such that the sheath is positioned at the desired location.

Before continuing, it should be noted that the catheter 10 may be implemented as an irrigated catheter. In an exemplary embodiment, the luer device 20 shown in FIG. 1 is used to open or close a flow path so that fluid is passed through Y-connector 18 and tubing 12 to tip assembly 14, for example, when the catheter 10 is also used for irrigation purposes. Tip assembly 14 may include one or more openings or irrigation ports 36 for passage of fluid from within tubing 12 to an exterior of tip assembly 14 when located in the body of a patient. Inner tube 24 forms a fluid lumen which connects directly to a plurality of openings that form irrigation ports 36, e.g., for saline irrigation.

The tip electrode 46 shown in FIG. 3 (and/or other locations in the tip assembly 14) may be formed with a plurality of openings that form irrigation ports 36 for irrigation. A central lumen 42 (in FIG. 2) is in fluid communication with luer 20 (shown in FIG. 1) on one end, and with irrigation ports 36 at the other end. Thus, an irrigation fluid, such as saline, may be injected through the inner tube 24. Tubing 24 may be formed, for example, by a braided polyimide tube that maintains the flow path through lumen in all orientations of tip assembly 14, without compromising the flexibility of tubing 12.

It is noted that although shown in the specific examples of FIG. 1 and FIG. 3, the catheter 10 is not limited to use with irrigated catheters, and hence in other embodiments, the fluid lines and irrigation ports shown and described herein need not be provided.

Figure 7A:
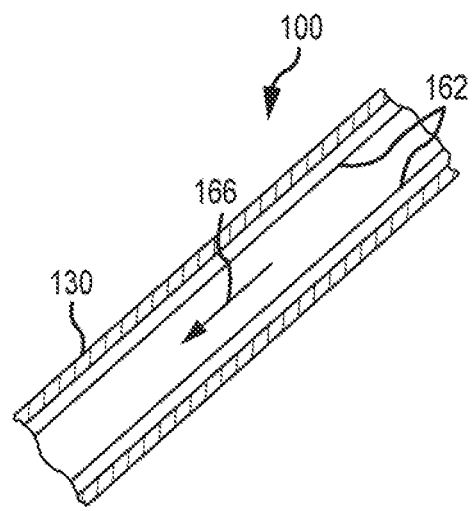
FIGS. 7A-B are magnified isometric views of the distal end portion of another embodiment of a catheter, the catheter having one or more channels formed therein for a magnetic fluid.
Figure 7B:
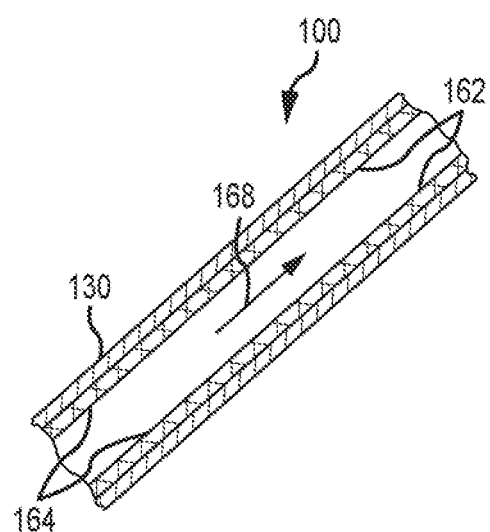

The distal portion of another embodiment of a magnetically guided catheter 100 is shown in FIGS. 7A-B, and is similar in many aspects to the catheter 10 described above. Like components and features of catheter 10 are indicated with like reference numbers in FIGS. 7A and 7B. Therefore, the description of like components may not be described again with reference to FIGS. 7A and 7B. Unlike catheter 10, catheter 100 includes channels 162 formed therein for a magnetic fluid 164 (FIG. 7B).

FIG. 7A shows the channels 162 as they may appear when the magnetic fluid 164 is evacuated or withdrawn (e.g., in the direction of arrow 166) to empty the channels 162. In FIG. 7B, the magnetic fluid 164 is shown as it may fill or partially fill the channels 162. According to such an embodiment, the magnetic fluid 164 may be retained in a reservoir (e.g., provided outside the patient's body and connected at the Y-connector 18 shown in FIG. 1). A suitable manual or electric pump/vacuum system may be used to provide the magnetic fluid 164 into the channels 162. The magnetic fluid 164 can thus be used to position the catheter tubing 112 and/or tip assembly 114 of the catheter 100, similarly to that described above for movable magnet 16 in catheter 10. The pump/vacuum may then be activated to evacuate the magnetic fluid 164 from the channels 162 when it is no longer needed (e.g., after positioning the catheter).

Advantageously, use of a magnetic fluid may be implemented without blocking or partially blocking the lumen of tubing 12. In addition, a magnetic fluid may be readily adaptable to automated means, such as the electric pump described above.

Figure 8A:
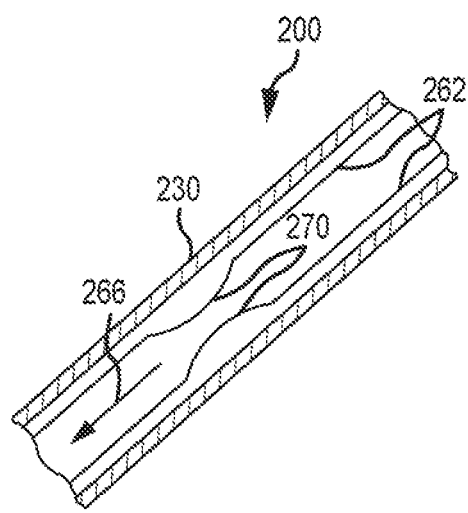
FIGS. 8A-B are magnified isometric views of the distal end portion of another embodiment of a catheter, the catheter having channels and one or more chamber formed therein for a magnetic fluid.
Figure 8B:
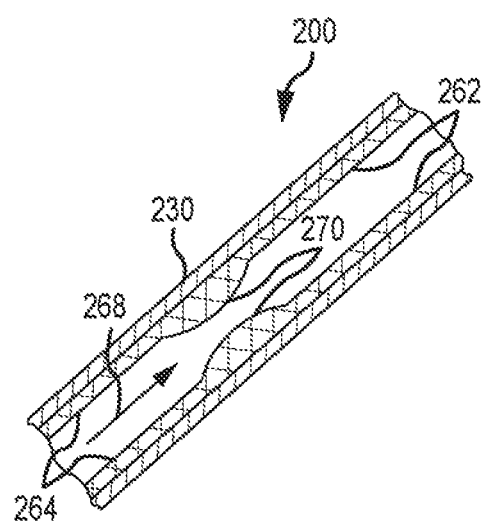

The distal portion of another embodiment of a magnetically guided catheter 200 is shown in FIGS. 8A-B, and is similar in many aspects to catheters 10 and 100 described above. Like components and features of catheters 10 and 100 are indicated with like reference numbers in FIGS. 8A and 8B. Therefore, the description of like components may not be described again with reference to FIGS. 8A and 8B.

Like catheter 100, catheter 200 also includes channels 262 for providing and evacuating a magnetic fluid 264 along the length of tubing 212. Unlike catheter 100, however, catheter 200 also includes at least one chamber 270 formed therein to receive the magnetic fluid. The chamber(s) 270 may be provided at predetermined positions along tubing 212 of the catheter 200 so that the magnetic fluid 264 pools and enhances operation when the magnetic field is applied.

In FIG. 8A, the magnetic fluid 264 has been withdrawn in a direction generally illustrated by arrow 266 through the channels 262 to a reservoir (not shown). The magnetic fluid 264 is shown in FIG. 8B as it may be provided in a direction generally illustrated by arrow 268 through the channels 262 to fill (or at least partially fill) the chamber(s) 270.

Advantageously, chamber(s) 270 may be spaced apart similarly to the permanent magnets 38 and 40 (described above for FIG. 2) and optionally used in place thereof to simplify construction and thereby reduce cost to manufacture the catheter.

It is noted that the embodiments described above with reference to FIGS. 7A and 7B and FIGS. 8A and 8B could just as easily be implemented with the magnetic fluid being provided in the central chamber of the catheters 100 and 200, rather than on the outer edge as shown. For example, the magnetic fluid may be provided in a separate lumen provided through the tubing of catheters 100 and 200. Or the magnetic fluid may be provided through the central lumen of the catheters 100 and 200.

While the invention has been described in terms of various specific embodiments, those skilled in the art will recognize that the invention can be practiced with modification within the spirit and scope of the claims.

What is claimed is:

1. A catheter, comprising:
   a flexible tubing with a proximal end, a distal end, and at least one shielded area;
   at least one movable magnet movable with respect to the flexible tubing at least one of: within the flexible tubing, inside the flexible tubing, and outside the flexible tubing;
   a control mechanism configured to position the at least one movable magnet inside the at least one shielded area to at least partially selectively de-activate the at least one movable magnet and further configured to position the at least one movable magnet outside the at least one shielded area to selectively re-activate the at least one movable magnet relative to an external magnetic field; and
   wherein the at least one movable magnet is responsive to the external magnetic field to position and guide the distal end of the flexible tubing to a desired location.

2. A catheter in accordance with claim 1, wherein the control mechanism is configured to be selectively activated from the proximal end of the flexible tubing.

3. A catheter in accordance with claim 2, wherein the control mechanism further includes a handle and a tether, wherein the tether couples on one end to the at least one movable magnet, the tether connected on the other end to a portion of the handle to move the at least one magnet along a longitudinal axis of the flexible tubing.

4. A catheter in accordance with claim 1, wherein the control mechanism is configured to move the at least one movable magnet inside the at least one shielded area to at least partially selectively de-activate the at least one movable magnet, and the control mechanism is configured to position the at least one movable magnet outside the at least one shielded area to selectively re-activate the at least one movable magnet relative to the external magnetic field.

5. A catheter in accordance with claim 1, wherein the control mechanism is configured to move the at least one shielded area over the at least one movable magnet to at least partially selectively de-activate the at least one movable magnet, and the control mechanism is configured to move the at least one shielded area away from the at least one movable magnet to selectively re-activate the at least one movable magnet relative to the external magnetic field.

6. A catheter in accordance with claim 1, further comprising at least one stationary magnet, the at least one stationary magnet remaining stationary relative to the flexible tubing.

7. A catheter in accordance with claim 1, further comprising at least one other movable magnet movable with respect to the flexible tubing at least one of: within the flexible tubing, inside the flexible tubing, and outside the flexible tubing.

8. A catheter in accordance with claim 1, further comprising a system selected from the group consisting of:
   a magnetic resonance imaging (MRI) system, an electromagnetically-based visualization/localization system, an impedance-based visualization/localization system, and a fluoroscopically-based imaging system configured to detect the flexible tubing and the at least one magnet; and wherein the at least one movable magnet comprises an electromagnet switchable from an active state to an inactive state relative to the external magnetic field, wherein the external magnetic field is coordinated with the system.

9. A catheter in accordance with claim 1, wherein the at least one movable magnet is removable from the flexible tubing for insertion of a fluid lumen or electrode assembly in lieu of the at least one movable magnet.

10. A catheter in accordance with claim 1, wherein the at least one movable magnet includes a first magnet and a second magnet spaced from the first magnet along the longitudinal axis of the flexible tubing.

11. A catheter in accordance with claim 1, further comprising a lumen passing through the at least one movable magnet, the lumen provided in fluid communication with at least one irrigation port at the distal end of the flexible tubing.

12. A catheter in accordance with claim 1, wherein the at least cine movable magnet includes a magnetic fluid.

13. A catheter in accordance with claim 12, further comprising at least one chamber in the flexible tubing, and wherein the magnetic fluid is at least partially selectively re-activated by at least partially filling at least one of the plurality of chambers with the magnetic fluid, and wherein the magnetic fluid is de-activated by at least partially emptying the magnetic fluid from the plurality of chambers.

14. A catheter in accordance with claim 1, wherein the flexible tubing is an introducer sheath configured to accept another catheter therethrough after positioning at the desired location, and the introducer sheath comprises a sheath selected from the group consisting of a precurved sheath, a uni-directional deflectable sheath, a bi-directional deflectable sheath, and an omni-directional deflectable sheath.

15. A catheter, comprising:
a flexible tubing with a proximal end and a distal end;
at least one magnet provided one of: within, inside, and outside of the flexible tubing;
a control mechanism configured to move the at least one magnet relative to the flexible tubing, the movement effected from the proximal end of the flexible tubing;
an active area of the flexible tubing, the at least one magnet moveable into the active area of the flexible tubing, and the at least one magnet responsive to an external magnetic field in the active area of the flexible tubing to position and guide the flexible tubing within a body of a patient; and
at least one shielded area of the flexible tubing, wherein the control mechanism is configured to position the at least one magnet relative to the at least one shielded area to selectively de-activate the at least one magnet when the at least one magnet is in the at least one shielded area.

16. A catheter accordance with claim 15, wherein the control mechanism includes a handle and a tether, the tether coupled to the at least one magnet, the tether connected on the other end to a portion of the handle of the catheter to move the at least one magnet along a longitudinal axis of the flexible tubing.

17. A catheter in accordance with claim 15, wherein the control mechanism is configured to robotically position at least a portion of the flexible tubing relative to the body of the patient without user intervention.

18. A method of guiding a catheter comprising:
providing at least one movable magnet within a flexible tubing of the catheter;
at least partially selectively de-activating the magnet with a positioning device at a proximal end of the flexible tubing by positioning the at least one magnet inside at least one shielded area of the flexible tubing;
at least partially selectively activating the at least one movable magnet with the positioning device at the proximal end of the flexible tubing by positioning the at least one movable magnet outside the at least one shielded area; and
applying an external magnetic field to the at least one movable magnet to position a distal end of the flexible tubing within a body of the patient.

19. A method in accordance with claim 18, wherein the at least one movable magnet moves inside the at least one shielded area, or the at least one shielded area moves over the at least one movable magnet.

20. A method comprising:
grossly positioning a sheath in a body of a patient;
activating a magnet in the sheath to fine tune positioning of the sheath within a particular area of the body of the patient, wherein the magnet is provided substantially co-axial to the sheath;
moving the magnet to various locations in the sheath and activating the magnet using an external magnetic field to position various portions of the sheath at desired locations within the body of the patient;
selectively de-activating the magnet by positioning the magnet in at least one shield area of the sheath;
determining the position of the magnet relative to the sheath, and the position of the sheath relative to a target tissue within the body of the patient; and
mapping the tissue geometry and moving the magnet to different positions within the sheath while activating and de-activating the external magnetic field, such that the sheath is positioned at the desired location.

* * * * *